(12) United States Patent
Raunio et al.

(10) Patent No.: US 9,721,377 B2
(45) Date of Patent: Aug. 1, 2017

(54) METHOD OF CHARACTERIZING CREPED MATERIALS

(71) Applicant: KEMIRA OYJ, Helsinki (FI)

(72) Inventors: Jukka-Pekka Raunio, Tampere (FI); Mikko Makinen, Espoo (FI); Henry Skoog, Roswell, GA (US)

(73) Assignee: KEMIRA OYJ, Helsinki (FI)

( * ) Notice: Subject to any disclaimer, the term of this patent is extended or adjusted under 35 U.S.C. 154(b) by 119 days.

(21) Appl. No.: 14/370,678

(22) PCT Filed: Jan. 4, 2013

(86) PCT No.: PCT/US2013/020304
§ 371 (c)(1),
(2) Date: Jul. 3, 2014

(87) PCT Pub. No.: WO2013/103831
PCT Pub. Date: Jul. 11, 2013

(65) Prior Publication Data
US 2014/0347358 A1 Nov. 27, 2014

Related U.S. Application Data

(60) Provisional application No. 61/583,829, filed on Jan. 6, 2012, provisional application No. 61/583,814, filed on Jan. 6, 2012.

(51) Int. Cl.
| | |
|---|---|
| *G06T 15/04* | (2011.01) |
| *G01B 11/30* | (2006.01) |
| *G01B 11/24* | (2006.01) |
| *G01N 33/34* | (2006.01) |
| *G06T 7/42* | (2017.01) |

(52) U.S. Cl.
CPC .............. *G06T 15/04* (2013.01); *G01B 11/24* (2013.01); *G01B 11/303* (2013.01); *G01N 33/346* (2013.01); *G06T 7/42* (2017.01); *G06T 2200/04* (2013.01); *G06T 2207/10152* (2013.01);
(Continued)

(58) Field of Classification Search
CPC .............................. G06T 15/04; G01B 11/303
See application file for complete search history.

(56) References Cited

U.S. PATENT DOCUMENTS

| | | |
|---|---|---|
| 5,654,799 A | 8/1997 | Chase |
| 2004/0010375 A1 | 1/2004 | Schomacker et al. |

(Continued)

FOREIGN PATENT DOCUMENTS

| | | |
|---|---|---|
| EP | 1666240 | 7/2006 |
| WO | 2010010229 A1 | 1/2010 |

OTHER PUBLICATIONS

Hansson et al. "Topography and reflectance analysis of paper surfaces using a photometric stereo method" © 2000 Society of Photo-Optical Instrumentation Engineers pp. 2555-2561.*

(Continued)

*Primary Examiner* — Tapas Mazumder
(74) *Attorney, Agent, or Firm* — Thomas Horstemeyer, LLP

(57) ABSTRACT

Methods of characterizing the topography of a surface of a creped material, devices for characterizing surface topography of a creped material, computer systems for characterizing surface topography of a creped material, and the like, are disclosed.

31 Claims, 5 Drawing Sheets

(52) U.S. Cl.
CPC ............... *G06T 2207/20056* (2013.01); *G06T 2207/30124* (2013.01); *G06T 2215/12* (2013.01)

(56) References Cited

U.S. PATENT DOCUMENTS

| | | | |
|---|---|---|---|
| 2004/0208390 A1* | 10/2004 | Jiang | A61B 5/0059 382/260 |
| 2005/0075801 A1 | 4/2005 | Skeps | |
| 2005/0145352 A1* | 7/2005 | Hermans | D21F 11/14 162/112 |
| 2006/0118993 A1* | 6/2006 | Awofeso | B31F 1/07 264/156 |
| 2006/0207735 A1 | 9/2006 | Blanz | |
| 2006/0214971 A1* | 9/2006 | Yamazaki | G06K 15/02 347/15 |
| 2006/0237156 A1 | 10/2006 | Shakespeare | |
| 2008/0013818 A1* | 1/2008 | Shakespeare | G01B 11/306 382/141 |
| 2009/0116697 A1 | 5/2009 | Shalaby et al. | |
| 2011/0304705 A1 | 12/2011 | Kantor et al. | |

OTHER PUBLICATIONS

Supplemental Search Report for PCT/US2013/020304 mailed Oct. 13, 2015.
Peter Hansson et al: "Topography and reflectance analysis of paper surfaces using a photometric stereo method", Optical Engineering, vol. 39, No. 9, Jan. 1, 2000, p. 2555.
Peter Hansson; "Topography and reflectance analysis of paper surfaces using a photometric stereo method"; Opt. Eng. 39(9) 2555-2561 (Sep. 2000); Society of Photo-Optical Instrumentation Engineers 2555.
Translation of Chinese Office Action for Application No. CN 201380004899.8; dated Nov. 14, 2016; State Intellectual Property Office of the P.R.C.

* cited by examiner

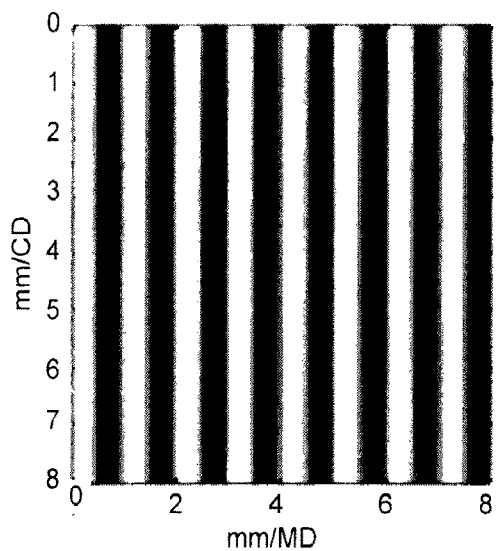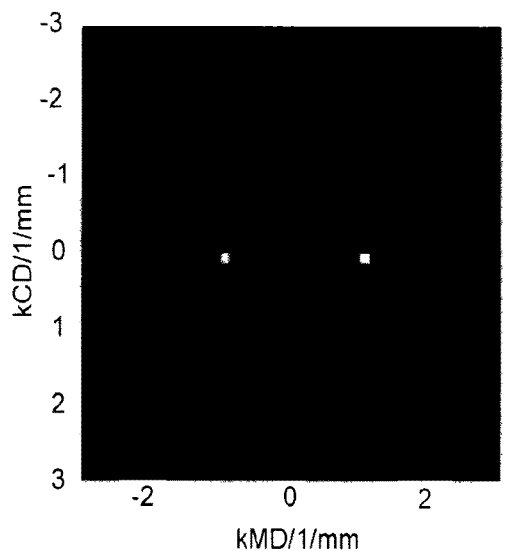
Figure 3A                Figure 3B
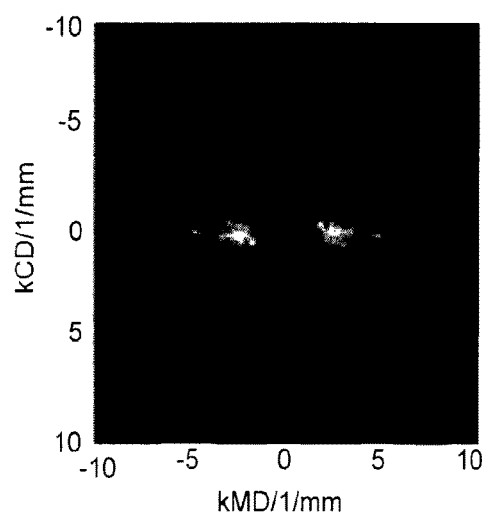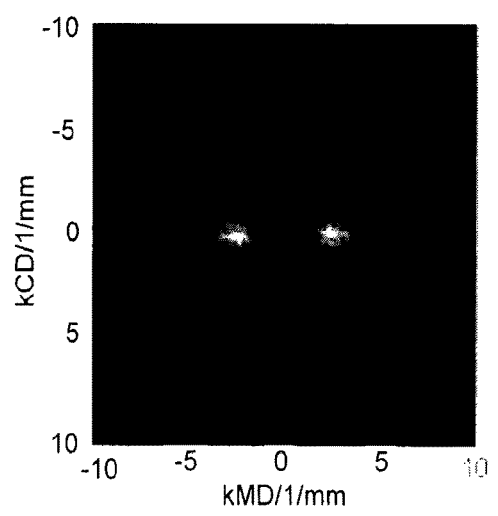
Figure 4A                Figure 4B

METHOD OF CHARACTERIZING CREPED MATERIALS

CROSS-REFERENCE TO RELATED APPLICATION

This application is the 35 U.S.C. §371 national stage of PCT Application No. PCT/US2013/020304, filed Jan. 4, 2013, which is herein incorporated by reference in its entirety and which also claims priority to, and the benefit of, U.S. provisional application entitled "Methods of Measuring Crepe Frequency" having Ser. No. 61/583,829, filed on Jan. 6, 2012 and U.S. provisional application entitled "Devices and Systems for Measuring Crepe Frequency" having Ser. No. 61/583,814, filed Jan. 6, 2012, both of which are herein incorporated by reference in their entirety.

BACKGROUND

1. Field of the Art

The present embodiments relate to characterizing surface topography of a creped material.

2. Description of Related Art

One of the operations that are considered in tissue production is the creping at the Yankee cylinder. The tissue sheet is adhered to a Yankee cylinder and then detached from the surface with a blade. As a result crepe bars are generated on the web. The creping process and crepe bars can have a significant effect on tissue quality properties, such as softness and production rate.

The description herein of certain advantages and disadvantages of known methods is not intended to limit the scope of the present disclosure. Indeed the present embodiments may include some or all of the features described above without suffering from the same disadvantages.

SUMMARY

In view of the foregoing, one or more embodiments include methods of characterizing the topography of a surface of a creped material, devices for characterizing topography of a surface of a creped material, computer systems for characterizing topography of a surface of a creped material, and the like.

At least one embodiment provides a method of characterizing the topography of the surface of a creped material, comprising: directing light onto a first surface of a creped material; obtaining at least two images of an identical portion of the first surface of the creped material, each image capturing the first surface illuminated from different directions; approximating from the images at least two surface normal vectors corresponding, respectively, to at least two portions of the first surface of the creped material; converting the at least two surface normal vectors to gradient image data; and analysing the gradient image data to characterize the topography of the first surface of the creped material.

At least one embodiment provides a method comprising: directing, by a computing device, light onto a first surface of a creped material; obtaining at least two images of an identical portion of the first surface of the creped material, each illuminated from a different direction; approximating, by the computing device, from the at least two images at least two surface normal vectors corresponding, respectively, to at least two portions of the first surface of the creped material; converting, by the computing device, the surface normal vectors to machine direction gradient image data; and analysing, by the computing device, the gradient image data to characterize the topography of the first surface of the creped material.

At least one embodiment provides a method comprising: at least one computing device; and a method application executable in the at least one computing device, the method application comprising: logic that directs light onto a first surface of a creped material; logic that obtains at least two images of an identical portion of the creped material, each image illuminated from different directions; logic that approximates from the at least two images at least two surface normal vectors corresponding, respectively, to at least two portions of the first surface of the creped material; logic that converts the surface normal vectors to machine direction gradient image data; and logic that analyses the gradient image data to characterize the topography of the first surface of the creped material.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3A illustrates an example of a sinusoidal wave in two dimensions, while FIG. 3B illustrates the Fourier Spectrum of the image in FIG. 3A.

FIG. 4A illustrates a Welch spectrum computed from the image of a tissue sheet, while FIG. 4B illustrates a Welch spectrum having the marking spot removed is shown.

FIG. 5A illustrates the power spectrum transformed to polar coordinates, while

DETAILED DESCRIPTION OF THE EMBODIMENTS

Figure 1:
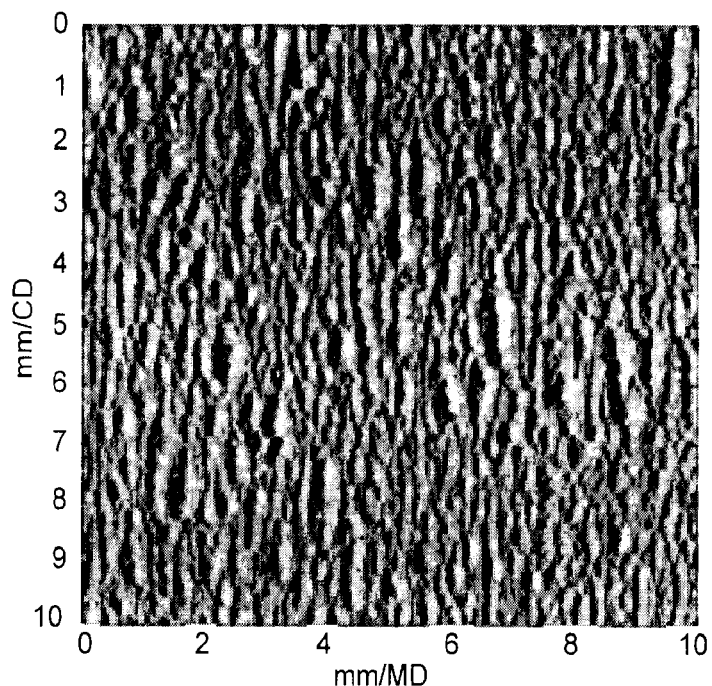
FIG. 1 illustrates an image of a tissue sheet after creping.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, paper chemistry, and the like, which are within the skill of the art. Such techniques are explained fully in the literature.

The examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms and phrases that shall be defined to have the following meanings unless a contrary intention is apparent.

DEFINITIONS

As used herein, the term "material" can refer to a paper or paper product.

As used herein, the terms "paper" or "paper product" (these two terms are used interchangeably) is understood to include a sheet material that contains paper fibers, and may also contain other materials. Suitable paper fibers include natural and synthetic fibers, for example, cellulosic fibers, wood fibers of all varieties used in papermaking, other plant fibers, such as cotton fibers, fibers derived from recycled paper; and the synthetic fibers, such as rayon, nylon, fiberglass, or polyolefin fibers. The paper product may be composed only of natural fibers, only of synthetic fibers, or a mixture of natural fibers and synthetic fibers. For instance, in the preparation of a paper product a paper web or paper material may be reinforced with synthetic fibers, such as nylon or fiberglass. As used herein, the terms "paper web" and "web" are understood to include both forming and formed paper sheet materials, papers, and paper materials containing paper fibers.

Paper can include, but is not limited to, writing papers and printing papers (e.g., uncoated mechanical, total coated paper, coated free sheet, coated mechanical, uncoated free sheet, and the like), industrial papers, tissue papers of all varieties, paperboards, cardboards, packaging papers (e.g., unbleached kraft paper, bleached kraft paper), wrapping papers, paper adhesive tapes, paper bags, paper cloths, toweling, wallpapers, carpet backings, paper filters, paper mats, decorative papers, disposable linens and garments, and the like.

Paper can include tissue paper products. Tissue paper products include sanitary tissues, household tissues, industrial tissues, facial tissues, cosmetic tissues, soft tissues, absorbent tissues, medicated tissues, toilet papers, paper towels, paper napkins, paper cloths, paper linens, and the like.

A tissue paper may be a feltpressed tissue paper, a pattern densified tissue paper, or a high bulk, uncompacted tissue paper. A tissue paper may be characterized as: creped or uncreped; of a homogeneous or multilayered construction; layered or non-layered (blended); and/or one-ply, two-ply, or three or more plies. Tissue paper may include soft and absorbent paper tissue products such as consumer tissue products.

Paper may refer to a paper product such as dry paper board, fine paper, towel, tissue, and newsprint products. Dry paper board applications include liner, corrugated medium, bleached, and unbleached dry paper board.

Paper can include carton board, container board, and special board/paper. Paper can include boxboard, folding boxboard, unbleached kraft board, recycled board, food packaging board, white lined chipboard, solid bleached board, solid unbleached board, liquid paper board, linerboard, corrugated board, core board, wallpaper base, plaster board, book bindery board, woodpulp board, sack board, coated board, and the like.

Discussion

The various exemplary embodiments described herein include methods of characterizing the topography (e.g., the three dimensional contours of a surface) of a material, devices useful for characterizing the topography of a material, computer systems useful for characterizing the topography of a material, and the like. In an embodiment, the topography of the surface of the material can be regular or irregular along the length or width of the material.

An exemplary material is one that has been creped (e.g., a creped tissue paper). For example, in some commercially-available bath tissue, a key operation in the tissue manufacturing process is the creping mechanism. Generally speaking in a typical creping process, a continuous paper web is adhered to a large heated rotating drum (Yankee cylinder). The drum dries the web by heating and evaporating the water from the paper web. The dried paper web is scraped off of the cylinder with a blade. As a result crepe folds are generated in the web, forming an irregular periodic waveform along the machine-direction of the web, with crepe folds extending generally in the cross-direction of the web. The geometry of the creped material is not necessarily uniform, varying in both the cross-direction and machine-direction of the material. The various methods, devices, and systems described herein can be used to characterize the surface topography associated with the creping.

An exemplary creped material is a sheet material that has a first surface, and an opposed second surface, and extends generally in a first direction, which is substantially parallel to the machine direction (MD) of a process that induces crepes into the material, and a second direction, which is substantially perpendicular to the MD of a process that induces crepes into the material. An exemplary creped material has a plurality of "crepe folds" or "crepe bars" that have a length that extends substantially in the second direction of the material (substantially perpendicular to the MD of the process). The surface of the creped material can be characterized, inter alia, by crepe bar length (e.g., length of the crepe along the second direction of the material), crepe bar width (e.g., width of the crepe along first direction of the material), crepe bar height (e.g., the height in a z-direction that is orthogonal to the surface of the material), and crepe frequency (e.g., the number of crepe bars over a specific length (e.g., a mm scale) as measured along the first direction of the material).

In an exemplary embodiment, the topography of a surface of a creped material can be characterized using images captured with an imaging system. In an exemplary embodiment, a first surface of a material can be exposed to one or more light sources that are directed at the first surface of the material from two or more different directions relative to the material. An imaging system can be used to capture two or more images of the surface, each captured while it is illuminated by one of the light sources. In each image, the light generates highlights and shadows which help to define the topography of the surface. Data from the images can be transformed (e.g., to a two dimensional spectrum (e.g., Welch spectrum)), smoothed, and analyzed, to provide a data set that can be used to characterize the crepes. For example, the crepe frequency of the material can be estimated from the data.

Figure 2:
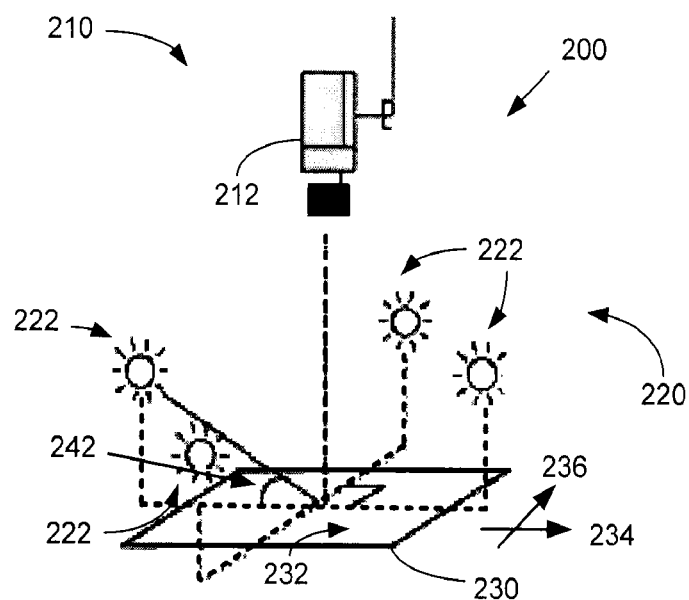
FIG. 2 illustrates a schematic of an exemplary embodiment of an imaging system.

Referring to FIG. 2, in an exemplary embodiment, an imaging system 200 can include a camera system 210 and a lighting system 220. The imaging system 200 may be configured to capture one or more images of a creped material 230, which extends, generally, in a first direction 234 and a second direction 236, and has a first surface 232 having a three-dimensional creped surface configuration. The camera system 210 may include a camera 212 that may be mounted in a relatively fixed configuration relative to the surface 232 of the creped material 230. The camera 212 may be, directed at the first surface 232 of the creped material 230, so that it may obtain one or more images of the creped material 230 as the lighting system 220 illuminates the creped material 230. In an embodiment, the camera 212 can be a digital camera. In an embodiment, the camera 212 can be disposed from about 10 to about 50 cm from the material. In an embodiment, the viewing window and angle of the camera 212 is constant, unchanged between successive images. In an embodiment, the image captured by the camera may have a rectangular shape. In an embodiment the image may comprise a plurality of pixels, such as an array of pixels.

In an exemplary embodiment, the lighting system 220 can include one or more light sources 222. Each light source 222 is oriented to illuminate the first surface 232 of the creped material 230 from a different direction. For example, the orientation of each light source 222 may be defined, at least in part, by a first angular orientation relative to the first 234 and second 236 direction of the creped material, and a second (tilt or slant) angular orientation 242, relative to the surface 232 of the creped material 230. In exemplary embodiments, the first angular orientation and the second angular orientation 242 of each of the light sources 222 may be any angle to provide a necessary or desired illumination effect on the creped material 230. For example, in an exemplary embodiment, the first angular orientation of a light source 222 may be from 0 degrees to about 180 degrees from the first direction 234 of the creped material 230. In an exemplary embodiment, the first angular orientation of a light source 222 may be from about 0 degrees to about 180 degrees from the second direction 236 of the creped material 230. In an exemplary embodiment, the second angular orientation 242 of a light source 222 may be from about 15 to about 85 degrees relative to the first surface 232 of the creped material 230. In an embodiment, the lighting system 220 can include two, three, four, or more light sources 222, each having a different orientation. In an embodiment, a single light source 222 can be used and can be moved to various positions to illuminate the first surface 232 of the creped material 230 from different orientations. In an embodiment, at least two lights 222 are provided, each light 222 being directed at a first surface 232 of the creped material 230, each light 222 disposed on opposite sides of the creped material 230 and directed at the creped material 230 at an angle (e.g., a slant angle of about 15 to 85 degrees or higher relative to the surface 232 creped material 230). In an embodiment, a first light 222 can be positioned at approximately 45 degrees to the first direction 234 of the creped material 230, and a second light can be positioned substantially orthogonal to the first light. In an embodiment, the lighting system 220 can include a lighting system 220 that can adjust (e.g., turn on and off, as well as adjust the intensity) the light sources 222 at certain times. In an embodiment, the one or more light sources 222 can be about 10 to 50 cm from the first surface 232 of the creped material 230. In an embodiment, the one or more light sources 222 can be any suitable source of illumination, including, for example, light emitting diodes (LEDS), for example, white LEDS. In an exemplary embodiment, the lighting system 220 comprises four LEDs, which are located at four corners of a tissue sample.

In an exemplary embodiment, a computing device (e.g., FIG. 8) can be in communication with the imaging system 200. For example, the computing device 10 may control various aspects of the lighting system 220 and/or various aspects of the camera system 210. For example, the computing device 10 may control the timing of when the light sources 222 are illuminated and/or when the camera system 210 captures digital images. In some embodiments, the computing device 10 may be configured to receive information from the lighting system 220. In some embodiments, the computing device 10 may be configured to receive information from the camera system 210.

In an embodiment, a method for characterizing the topography of a surface of a creped material includes directing light onto a first surface of the material from two or more directions. As the creped material is illuminated by the light from a particular direction, an imaging system captures an image of the first surface of the material. In exemplary embodiments, the imaging system is configured so that that it captures successive images of an identical portion of the surface of the creped material (and from the same direction), while it is illuminated from different lighting perspectives. Each of the different lighting perspectives generates highlights and shadows on different areas of the creped surface of the material, depending on the orientation of the light source. The measured light intensity for two or more images (each illuminated from a different direction) of the same portion of the first surface of the material, can provide information regarding the surface of the material. Using the information captured in the image, each pixel or group of pixels may be assigned one or more data values, including, for example, a gray scale value, a surface normal vector, and/or a gradient value. This data can provide sufficient information to determine, for example, surface orientation of the creped material corresponding to each portion (e.g., pixel) of the image. For example, the reflected light captured in two or more overlayed pixels can be used to approximate a surface normal vector for any portion of the creped material corresponding to that pixel. The term "surface normal" refers to a vector that is perpendicular to the tangent plane of the first surface of the creped material at a particular surface location. Using the surface normal vectors, one can characterize the topography in the surface of the creped material. For example, the image or series of successive images corresponding to a material, can be converted to an array (or arrays) of pixels. Each pixel can be assigned a surface normal vector. The array of surface normal vectors can help to characterize contours of the surface, e.g., the locations where the surface is ridged or creped can be identified and characterized.

In an exemplary embodiment, the surface normal vectors can be converted or correlated to gradient image data. For example, in an embodiment, the gradient image data of each pixel measures the change in value of the surface normal vectors of that location in the original image when comparing in a given direction. In an embodiment, the surface normal vector includes x component (MD), y component (CD), and z component. The MD gradient image can be computed by dividing the x (MD) component by z component for each pixel.

The gradient image data can be analyzed to characterize the topography of the creped material. In an embodiment, a two dimensional Fourier transform can be computed from the gradient image data. In an embodiment, the two-dimensional Fourier transform can convert the spatial gradient image data into frequency space. The Fourier transform of f(x) is denoted as F(k) and it describes the amplitude and phase for each frequency and orientation of two dimensional sinusoidal wave so that when summed they produce f(x). In other words, the transformation assigns a series of sine waves to the gradient image data such that the sum of the amplitudes of the sine waves corresponds to the grey scale values of the individual pixels in the original gradient image.

A two dimensional Fourier spectrum can show the variance and orientation of each frequency from the image. Creping is approximately a waveform where the wavelength varies locally. Thus, a power spectrum, which is reliable for the wavelength of periodic waves found from the image, can be selected to further analyze the Fourier spectrum.

In an exemplary embodiment, a two dimensional power spectrum can be computed from the two dimensional Fourier transform. In an embodiment, the two dimensional power spectrum can be computed by calculating the sum of the squared amplitudes of the sine waves functions, where the value of the amplitudes represents the "power".

Practically speaking, for a given material, the creping structures do not necessarily have a uniform structure (e.g., orientation, wavelength, etc.). In addition, the length of the crepe folds may be relatively small and varied. These phenomena may decrease the accuracy of wavelength estimation from the power spectrum, where the high variance marking spots widens in kMD and kCD directions. Regular marking spots may produce higher intensity spots in the power spectrum. The term "marking spots" refers to areas where the difference between the original and smoothed pixel values are at a maximum.

Creping does not necessarily form perfectly sinusoidal waves in the material so regular marking spot patterns are not formed through creping. Therefore, the marking spots can be removed from the power spectrum to find the "true" crepe frequency of the material.

In an embodiment, the two dimensional power spectrum can be smoothed to produce a smoothed two dimensional power spectrum. Smoothing can be used to remove the unwanted spectral peaks (e.g., noise such as marking spots) caused by the equipment used in the tissue of paper machine.

In an exemplary embodiment, the smoothing can be accomplished by obtaining a two dimensional filtered power spectrum (e.g., two dimensional median filtered power spectrum). Two dimensional filtering includes replacing each point with a value (e.g., a median value) of the values of the points that are adjacent on a two dimensional plane. In an embodiment, the filter can be a non-linear smoothing method, in which the current point is replaced in the image by the median of the values in its neighborhood. Then a ratio of an initial power spectrum to the filtered power spectrum is determined for each point in the spectrum. As a result, the intensity of the noise is higher than the other variations in the spectrum. The marking spots can be identified using a threshold level that peaks should not exceed. In an embodiment, the threshold level can be based on the material used, the dimensions of the crepes, and the like. The exact locations of spectral peak corresponding to the noise can be estimated by fitting a second order two dimensional polynomial (e.g., or other appropriate fitting scheme) around the maximum value of the peak of the noise. The values around the marking spots can be replaced with a value determined from the values of power spectrum in its neighborhood (e.g., determined by the mean, median or mode). In an embodiment, the term "neighborhood" refers to one or more points adjacent a given point. Thus, the power spectrum can be smoothed to remove noise such as that from marking spots.

In an exemplary embodiment, the power spectrum can be computed and smoothed with the Welch method (although other methods could be used), which decreases the effect of measurement noise by calculating the spectrum as an average over several, possibly overlapping samples. In an embodiment, each Fourier transform can be windowed with a Welch window before the computation of the Welch spectrum, where windowing decreases the spectral side lobes caused by the finite-sample Fourier transform.

In an embodiment, once the power spectrum is smoothed, a one dimensional probability distribution can be estimated by transforming the smoothed two dimensional power spectrum to a polar coordinate system to form a polar coordinate system smoothed power spectrum. In a polar coordinate system, the elements (x, y) are represented as pairs of angle $\theta$ and distance k from the origin. The transformation can be performed using the following formula: $k=(x^2+y^2)^{1/2}$ and $\phi=\arctan(y/x)$.

In an embodiment, the amount of variance can be held constant for the transformation of the power spectrum to a polar coordinate system. However, the polar coordinates are unevenly spaced compared to the Cartesian coordinate system and the intensity values of the power spectrum from Cartesian coordinate system cannot been used directly. Thus, the intensity values in polar coordinate system are interpolated from the original power spectrum. Finally, the one dimensional crepe frequency distribution is computed by summing the variances from the power spectrum between the angles of about −45 and +45 degrees together.

In an embodiment, a crepe frequency of the material can be estimated by determining a measure (e.g., a mean, a mode, or a median) of the one dimensional probability distribution. In an embodiment, the median value computed from the crepe frequency distribution is an estimate for the crepe frequency of the material. In an embodiment, a crepe frequency of the material can be estimated from the one dimensional probability distribution within the range of 0 to 254 crepe bars per inch.

Thus, an exemplary embodiment of the present disclosure can use images acquired of the topography of a surface of the creped material to determine the characteristics (e.g., crepe frequency) of the creped material.

Figure 8:
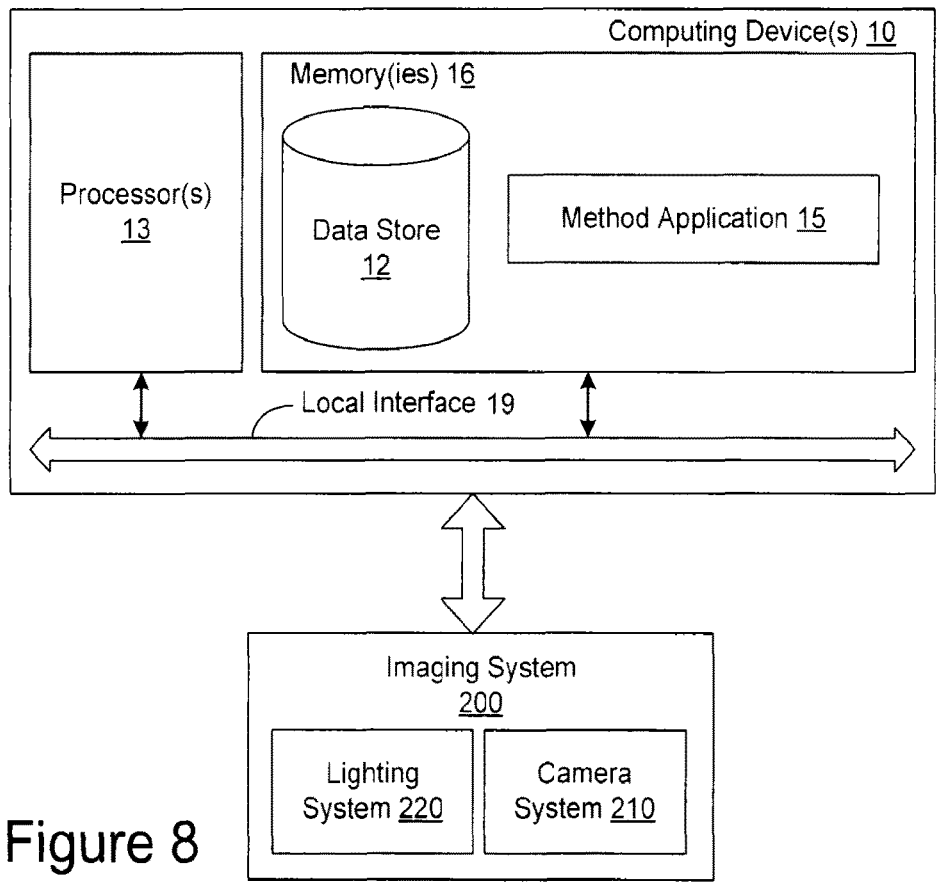
FIG. 8 is a schematic of a measurement system including a computer device.

Referring to FIG. 8, in an embodiment, the imaging system 200 may be in communication with the computer device 10. In particular, the camera system 210 and the lighting system 220 may be communication with the computer device 10.

In an exemplary embodiment, one or more aspects of the method of analyzing the topography in a material can be implemented using software and/or hardware as described herein.

With reference to FIG. 8, shown is a schematic block diagram of a computing device 10 according to various embodiments of the present disclosure. The computing device 10 includes at least one processor circuit, for example, having a processor 13 and a memory 16, both of which are coupled to a local interface 19. To this end, the computing device 10 may comprise, for example, at least one server computer or like device. The local interface 19 may comprise, for example, a data bus with an accompanying address/control bus or other bus structure as can be appreciated.

Stored in the memory 16 are both data and several components that are executable by the processor 13. In particular, stored in the memory 16 and executable by the processor 13 are a method application 15 and/or other applications. Also stored in the memory 16 may be a data store 12 and other data. In addition, an operating system may be stored in the memory 16 and executable by the processor 13.

It is understood that there may be other applications that are stored in the memory 16 and are executable by the processor 13 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Delphi®, Flash®, MATLAB, or other programming languages.

A number of software components can be stored in the memory 16 and are executable by the processor 13. In this respect, the term "executable" means a program file that is in a form that can ultimately be run by the processor 13. Examples of executable programs may be, for example, a compiled program that can be translated into machine code in a format that can be loaded into a random access portion of the memory 16 and run by the processor 13, source code that may be expressed in proper format such as object code that is capable of being loaded into a random access portion of the memory 16 and executed by the processor 13, or source code that may be interpreted by another executable program to generate instructions in a random access portion of the memory 16 to be executed by the processor 13, etc. An executable program may be stored in any portion or component of the memory 16 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 16 is defined herein as including both volatile and nonvolatile memory and data storage components. Volatile components are those that do not retain data values upon loss of power. Nonvolatile components are those that retain data upon a loss of power. Thus, the memory 16 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 13 may represent multiple processors 13 and the memory 16 may represent multiple memories 16 that operate in parallel processing circuits, respectively. In such a case, the local interface 19 may be an appropriate network that facilitates communication between any two of the multiple processors 13, between any processor 13 and any of the memories 16, or between any two of the memories 16, etc. The local interface 19 may comprise additional systems designed to coordinate this communication, including, for example, performing load balancing. The processor 13 may be of electrical or of some other available construction.

Although the method application 15 and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Figure 9:
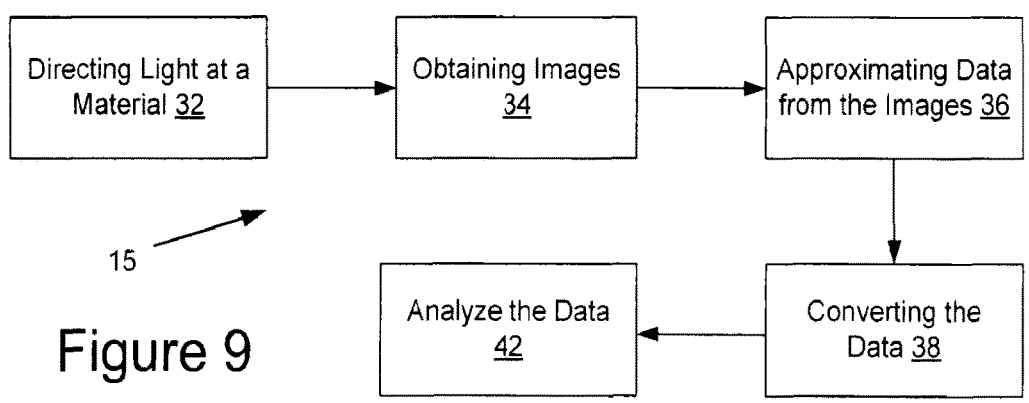
FIG. 9 is a flow chart of an example of a measuring topography in a material.

Referring to FIG. 9, in an exemplary embodiment, a method application 15 can be used for characterizing the topography of a surface of a creped material. In general, the method application 15 corresponds to any of the exemplary methods of characterizing the topography of a surface of a creped material as described herein. In an exemplary embodiment, a step 32 of the method application 15 includes directing light at a surface of a creped material. The method application 15 may generate instruction communicated to the imaging system 200 regarding various aspects of the lighting step. For example, the method application 15 may provide instruction regarding intensity or timing of the lighting, for each of the lighting sources in the device. The method application 15 may also include the step 34 of obtaining two or more successive images of the surface of the creped material. The method application 15 may generate instruction communicated to the imaging system 200 regarding various aspects of the imaging step. For example, the method application 15 may provide instruction to the imaging system 200 regarding the timing of capturing the images (e.g., in coordination with lighting instruction). The method application 15 will also receive the two or more images captured by the imaging system 200. The method application 15 further includes the step 36 of capturing and/or approximating data from the received images. For example, each image may include an array of pixels, each providing information about the image, e.g., a measurement of reflected light. The method application 15 may capture that received information, and/or calculate additional data based on the received information. For example, the method application 15 may approximate a surface normal vector for a pixel based upon the reflected light data from two successive images. The method application 15 may assign each pixel one or more data points. The method application 15 further includes the step 38 of converting the data from step 36. For example, the data from step 36 can be converted to gradient image data. The method application 15 further includes the step 42 of analysing the data generated in step 38, to characterize the surface of the creped material. For example, the gradient image data for the images can be analysed to determine a crepe frequency of the material. Each of these features is described herein in more detail, specifically, in regard to the discussion regarding analyzing topography of a creped material.

Although the flowchart of FIG. 9 shows a specific order of execution, it is understood that any number of counters, state variables, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the method application 15 and/or application(s), that comprises software or code can be embodied in any non-transitory computer-readable medium for use by or in connection with an instruction execution system such as, for example, a processor 13 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

EXAMPLES

Now having described the embodiments, in general, the examples describe some additional embodiments. While embodiments are described in connection with the examples and the corresponding text and figures, there is no intent to limit embodiments of the disclosure to these descriptions. On the contrary, the intent is to cover all alternatives, modifications, and equivalents included within the spirit and scope of exemplary embodiments.

Example 1

In this example, three sample strips were taken from a bath grade tissue web that was manufactured on a tissue machine having a width of 4500 mm (CD). The samples were cut from the same web and the interval of samples in the MD was approximately 10 meters. The average basis weight of each sample was 15 g/m$^2$. Each sample was cut across the web, where each sample includes one crosscut strip. Each sample was measured offline with an imaging device. The offline profiles were aligned uniformly in CD to maximize the correlation.

Image Measurements:

Each crosscut strip was imaged with the imaging system that captured light reflectance images. The imaging device included a fixed digital camera and four light sources (light emitting diodes (LED)) at a slant angle of 55 degrees. Images of each bath tissue sample were collected across the CD width of the sample, each image capturing a 300 mm wide portion of the sample in the CD. Each portion of the web was imaged four times—each time illuminated by one of the four light sources. The resolution of image was 0.01 mm/pixel in both the CD and MD, and the size of the image sensor was 5202×3464 pixel (MD×CD). Thus, the size of the single image was 52 mm×35 mm. An example of the image captured with the imaging device from one of the tissue sheet samples is shown in FIG. 1.

Estimating the Crepe Frequency from Images:

A two dimensional power spectrum was generated from the digital images of each tissue sample material. The crepe frequency was computed from a two dimensional power spectrum of the digital images for the sample. The spectrum was computed with the Welch method. [Hayes, M., "Statistical Digital Signal Processing and Modeling", John Wiley & Sons, USA, 1996, which is incorporated herein by reference in its entirety]. The Fourier transform was windowed with a Welch window before the computation of Welch spectrum, where windowing decreased the spectral side lobes caused by the finite-sample Fourier transform.

FIG. 3B illustrates the two dimensional Fourier spectrum computed from the sinusoidal wave (FIG. 3A) having a wavelength of 1 mm. The bright spots in the Fourier spectrum describe the frequency of the most common (highest variance) wavelength in the image. The Fourier spectrum is symmetrical with respect to the origin, therefore, the wavelength of the sinusoidal wave is described as two bright spots.

FIG. 4A illustrates a Welch spectrum computed from the image of a tissue sheet, while FIG. 4B illustrates a Welch spectrum having the marking spot removed. The location of spots from the Welch spectrum was determined so that the marking spots could be removed, as shown in FIG. 4B.

Figure 5A:
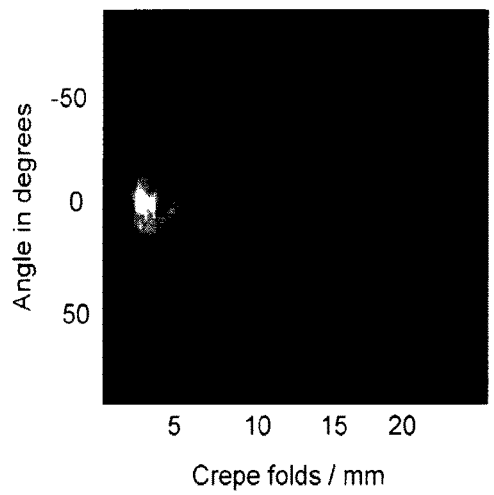
Figure 5B:
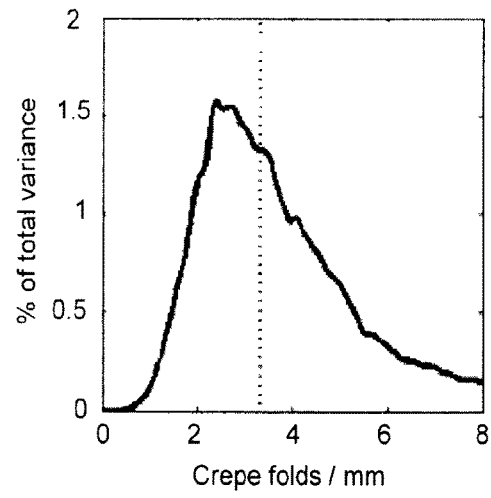
FIG. 5B illustrates a graph of a one dimensional probability distribution based on FIG. 5A.

The crepe frequency of the tissue sample was obtained by transforming the power spectrum to polar coordinate system. FIG. 5A illustrates the power spectrum transformed to polar coordinates. Only the angles between the −90 and +90 are shown. The one dimensional crepe frequency distribution (FIG. 5B) is computed by summing the variances from an interval (e.g., about −45 to 45) degrees). The dashed vertical line shows the median value computed from the one dimensional crepe frequency distribution.

Figure 6A:
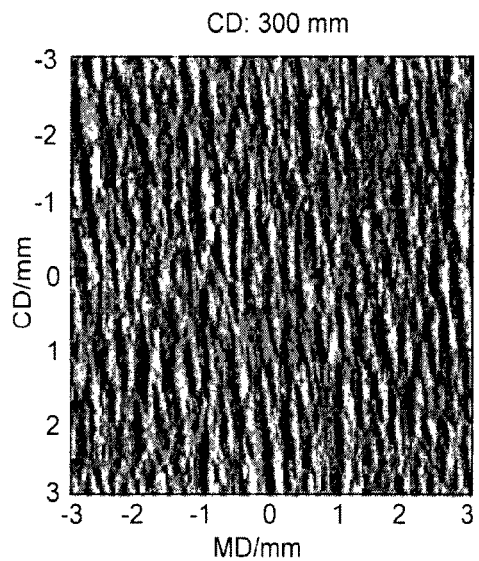
FIG. 6A illustrates an image from the CD location at 300 mm and FIG. 6B illustrates an image from the CD at 2700 mm.
Figure 6B:
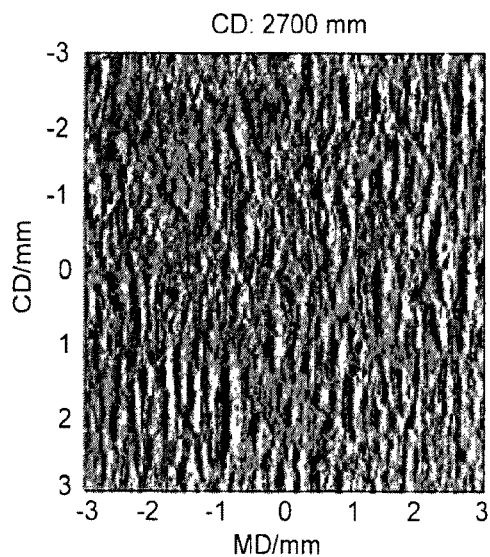
Figure 7:
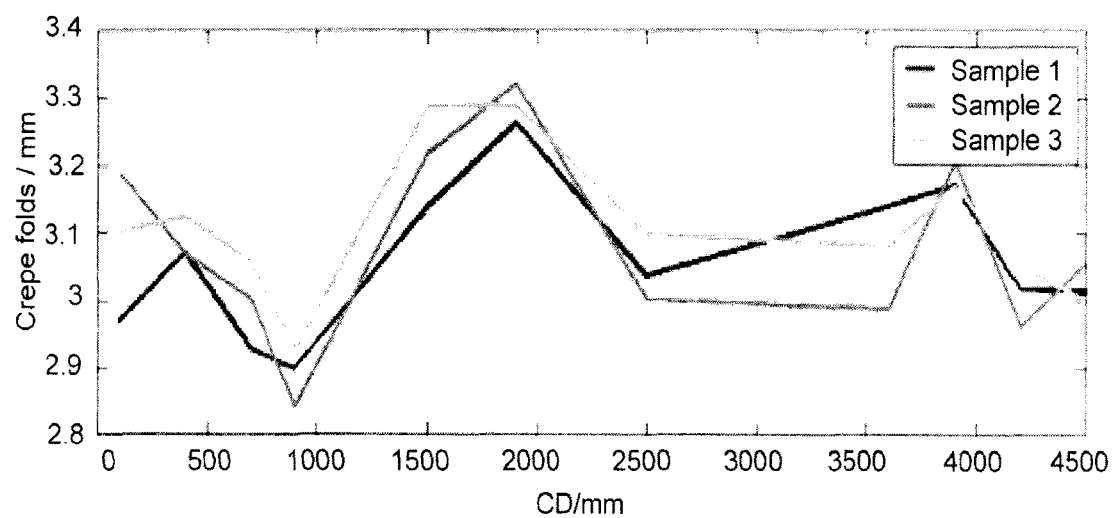
FIG. 7 illustrates a graph of the crepe frequency profiles measured from the bath tissue.

The resulting crepe frequency profiles from each bath tissue sample are shown in FIG. 7, showing variation in the frequency from one side of the web to the other. In these samples, the crepe fold frequency (# of crepe folds per mm) varied between 2.9 and 3.3. Exemplary images of bath tissue sample 2 corresponding to the CD location of 300 mm is shown in FIG. 6A and from CD location of 2700 mm is shown in FIG. 6B.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

The invention claimed is:

1. A computer-implemented method of programmatically characterizing a surface topography of a creped material produced by a creping mechanism, comprising:
  positioning one or more light sources configured to illuminate a first surface of the creped material from two or more positions, wherein each position of the two or more positions is characterized by a tilt angle relative to a machine direction (MD) and a crepe direction (CD) of the creped material and a slant angle relative to the first surface of the creped material;
  accessing at least two images that capture an identical portion of the first surface of the creped material, wherein each of the at least two images that capture the first surface is illuminated from a different direction, wherein a first image of the at least two images is illuminated from a first position of the two or more positions and a second image of the at least two images is illuminated from a second position of the two or more positions;
  programmatically approximating from the at least two images at least two surface normal vectors corresponding, respectively, to at least two portions of the first surface of the creped material;
  converting the at least two surface normal vectors to generate a gradient image; and
  analysing the gradient image to characterize a topography of the first surface of the creped material, where control of the creping mechanism is adjusted based on the characterized topography.

2. The computer-implemented method of claim 1, wherein analysing the gradient image comprises:
  generating a two dimensional Fourier transform from the gradient image data; and
  generating a two dimensional power spectrum from the two dimensional Fourier transform.

3. The computer-implemented method of claim 2, wherein computing the two dimensional power spectrum comprises smoothing the two dimensional power spectrum to generate a smoothed two dimensional power spectrum.

4. The computer-implemented method of claim 3, wherein smoothing the two dimensional power spectrum comprises:
  obtaining a filtered two dimensional power spectrum;
  determining a ratio of an initial power spectrum value to a filtered two dimensional power spectrum value for each point in the two dimensional power spectrum;
  comparing the ratio determined for each point in the two dimensional power spectrum to a threshold value, wherein points above the threshold value are a marking spot;
  estimating locations of spectral peak by fitting a second order two dimensional polynomial around a maximum value of peaks, wherein at least one of the spectral peaks corresponds to the marking spot; and
  replacing the values around the marking spot with the values of the two dimensional power spectrum in its neighbourhood.

5. The computer-implemented method of claim 3, wherein smoothing the two dimensional power spectrum comprises:
  obtaining a two dimensional median filtered power spectrum;
  determining a ratio of an initial power spectrum value to a two dimensional median filtered power spectrum value for each point in the two dimensional power spectrum;
  comparing the ratio determined for each point in the two dimensional power spectrum to a threshold value, wherein points above the threshold value are a marking spot;
  estimating locations of spectral peak by fitting a second order two dimensional polynomial around a maximum value of peaks, wherein at least one of the spectral peaks corresponds to the marking spot; and
  replacing the values around the marking spot with the values of the two dimensional power spectrum in its neighbourhood.

6. The computer-implemented method of claim 4, wherein analysing the gradient image comprises:

transforming the smoothed two dimensional power spectrum to a polar coordinate system creating a polar coordinate system smoothed power spectrum; and estimating a one dimensional probability distribution from the polar coordinate system smoothed power spectrum.

7. The computer-implemented method of claim 6, wherein transforming comprises estimating the one dimensional probability distribution by summing values from the polar coordinate system smoothed power spectrum between the angles of about −45 and +45 degrees together in the polar coordinate system.

8. The computer-implemented method of claim 6, wherein analysing the gradient image comprises determining a crepe frequency of the material by determining a measure of the one dimensional probability distribution.

9. The computer-implemented method of claim 8, wherein the measure is a mean, a mode, or a median, of the one dimensional probability distribution.

10. The computer-implemented method of claim 6, wherein analysing comprises determining a crepe frequency of the material by computing a median of the one dimensional probability distribution.

11. The computer-implemented method of claim 6, wherein analysing the gradient image comprises determining a crepe frequency of the material by computing the one dimensional probability distribution within a range of 0 to 254 crepe bars per inch.

12. A computer-implemented method of characterizing a surface topology of a creped material produced by a creping mechanism, comprising:

positioning, by a computing device, one or more light sources configured to illuminate a first surface of the creped material from two or more positions, wherein each position of the two or more positions is characterized by a tilt angle relative to a machine direction (MD) and a crepe direction (CD) of the creped material and a slant angle relative to the first surface of the creped material;

obtaining, by the computing device, at least two images of an identical portion of the first surface of the creped material, each of the at least two images illuminated from a different direction, wherein a first image of the at least two images is illuminated from a first position of the two or more positions and a second image of the at least two images is illuminated from a second position of the two or more positions;

approximating, by the computing device, from the at least two images at least two surface normal vectors corresponding, respectively, to at least two portions of the first surface of the creped material;

converting, by the computing device, the at least two surface normal vectors to generate a machine direction gradient image; and analysing, by the computing device, the gradient image to characterize a topography of the first surface of the creped material, where control of the creping mechanism is adjusted based on the characterized topography.

13. The computer-implemented method of claim 12, wherein analysing the gradient image comprises:

generating, by the computing device, a two dimensional Fourier transform from the machine direction gradient image; and generating, by the computing device, a two dimensional power spectrum from the two dimensional Fourier transform.

14. The computer-implemented method of claim 13, wherein computing the two dimensional power spectrum comprises: smoothing, by the computing device, the two dimensional power spectrum to generate a smoothed two dimensional power spectrum.

15. The computer-implemented method of claim 14, wherein smoothing the two dimensional power spectrum comprises:

obtaining a two dimensional filtered power spectrum;

determining a ratio of an initial power spectrum value to a filtered two dimensional power spectrum value for each point in the two dimensional power spectrum;

comparing the ratio determined for each point in the two dimensional power spectrum to a threshold value, wherein points above the threshold value are a marking spot;

estimating locations of spectral peak by fitting a second order two dimensional polynomial around a maximum value of peaks, wherein at least one of the spectral peaks corresponds to the marking spot; and replacing the values around the marking spot with the values of the two dimensional power spectrum in its neighbourhood.

16. The computer-implemented method of claim 14, wherein smoothing the two dimensional power spectrum comprises:

obtaining a two dimensional median filtered power spectrum;

determining a ratio of an initial power spectrum value to a two dimensional median filtered power spectrum value for each point in the two dimensional power spectrum;

comparing the ratio determined for each point in the two dimensional power spectrum to a threshold value, wherein points above the threshold value are a marking spot;

estimating locations of spectral peak by fitting a second order two dimensional polynomial around a maximum value of peaks, wherein at least one of the spectral peaks corresponds to the marking spot; and replacing the values around the marking spot with the values of the two dimensional power spectrum in its neighbourhood.

17. The computer-implemented method of claim 12, wherein analysing comprises:

transforming a smoothed two dimensional power spectrum to a polar coordinate system creating a polar coordinate system smoothed power spectrum; and estimating a one dimensional probability distribution from the polar coordinate system smoothed power spectrum.

18. A system for characterizing a surface topology of a creped material produced by a creping mechanism, comprising:

a lighting system, comprising one or more light sources configured to illuminate a first surface from two or more positions, wherein each position of the two or more positions is characterized by a tilt angle relative to a machine direction (MD) and a crepe direction (CD) of the creped material and a slant angle relative to a first surface of the creped material;

at least one computing device; and program instructions executable in the at least one computing device that, when executed, cause the at least one computing device to:

direct light onto the first surface of a creped material from at least a first position of the two or more positions and a second position of the two or more positions;

obtain at least two images of an identical portion of the creped material, wherein a first image of the at least two images is illuminated from the first position and a second image of the at least two images is illuminated from the second position;

approximate from the at least two images at least two surface normal vectors corresponding, respectively, to at least two portions of the first surface of the creped material;

convert the at least two surface normal vectors to generate a machine direction gradient image; and analyse the machine direction gradient image to characterize a topography of the first surface of the creped material, where control of the creping mechanism is adjusted based on the characterized topography.

19. The system of claim 18, further comprising the program instructions executable in the at least one computing device that, when executed, cause the at least one computing device to:

generate a two dimensional Fourier transform from the gradient image; and generate a two dimensional power spectrum from the two dimensional Fourier transform.

20. The system of claim 19, wherein computing the two dimensional power spectrum comprises smoothing the two dimensional power spectrum to generate a smoothed two dimensional power spectrum.

21. The system of claim 20, wherein smoothing the two dimensional power spectrum comprises:

obtaining a two dimensional filtered power spectrum;

determining a ratio of an initial power spectrum value to a filtered two dimensional power spectrum value for each point in the two dimensional power spectrum;

comparing the ratio determined for each point in the two dimensional power spectrum to a threshold value, wherein points above the threshold value are a marking spot;

estimating locations of spectral peak by fitting a second order two dimensional polynomial around a maximum value of peaks, wherein at least one of the spectral peaks corresponds to the marking spot; and replacing the values around the marking spot with the values of the two dimensional power spectrum in its neighbourhood.

22. The system of claim 20, wherein smoothing the two dimensional power spectrum includes:

obtaining a two dimensional median filtered power spectrum;

determining a ratio of an initial power spectrum value to a two dimensional median filtered power spectrum value or each point in the two dimensional power spectrum;

comparing the ratio determined for each point in the two dimensional power spectrum to a threshold value, wherein points above the threshold value are a marking spot;

estimating locations of spectral peak by fitting a second order two dimensional polynomial around a maximum value of peaks, wherein at least one of the spectral peaks corresponds to the marking spot; and replacing the values around the marking spot with the values of the two dimensional power spectrum in its neighbourhood.

23. The system of claim 18, further comprising the program instructions executable in the at least one computing device that, when executed, cause the at least one computing device to:

transform a smoothed two dimensional power spectrum to a polar coordinate system creating a polar coordinate system smoothed power spectrum; and estimate a one dimensional probability distribution from the polar coordinate system smoothed power spectrum.

24. The system of claim 23, further comprising the program instructions executable in the at least one computing device that, when executed, cause the at least one computing device to estimate the one dimensional probability distribution by summing values from the polar coordinate system smoothed power spectrum between the angles of about −45 and +45 degrees together in the polar coordinate system.

25. The system of claim 23, further comprising the program instructions executable in the at least one computing device that, when executed, cause the at least one computing device to analyse by determining a crepe frequency of the material by determining a measure of the one dimensional probability distribution.

26. The system of claim 25, wherein the measure is a mean, a mode, or a median, of the one dimensional probability distribution.

27. The system of claim 23, further comprising the program instructions executable in the at least one computing device that, when executed, cause the at least one computing device to analyse by determining a crepe frequency of the material by computing a median.

28. The system of claim 23, further comprising the program instructions executable in the at least one computing device that, when executed, cause the at least one computing device to analyse by determining a crepe frequency of the material by computing the one dimensional probability distribution within a range of 0 to 254 crepe bars per inch.

29. A computer-implemented method of programmatically characterizing a surface topography of a creped material produced by a creping mechanism, comprising:

positioning one or more light sources configured to illuminate a first surface of the creped material from two or more positions, wherein each position of the two or more positions is characterized by a tilt angle relative to a machine direction (MD) and a crepe direction (CD) of the creped material and a slant angle relative to the surface of the creped material, wherein a first position of the two or more positions has a first tilt angle and a second position of the two or more positions has a second tilt angle orthogonal to the first tilt angle;

accessing at least two images that capture an identical portion of the surface of the creped material, wherein each of the at least two images capturing the surface is illuminated from a different direction, wherein a first image of the at least two images is illuminated from a first position of the two or more positions and a second image of the at least two images is illuminated from a second position of the two or more positions;

programmatically approximating from the at least two images at least two surface normal vectors corresponding, respectively, to at least two portions of the surface of the creped material;

converting the at least two surface normal vectors to generate a gradient image;
analysing the gradient image to characterize a topography of the surface of the creped material by:
computing a two dimensional Fourier transform from the gradient image;
computing a two dimensional power spectrum from the two dimensional Fourier transform; and
smoothing the two dimensional power spectrum to generate a smoothed two dimensional power spectrum; and
causing information associated with a characterization of the topography of the surface of the creped material to be rendered in a display device, wherein the information comprises the smoothed two dimensional power spectrum, where control of the creping mechanism is adjusted based on the characterization of the topography.

30. A computer implemented method of characterizing a surface topology of a creped material produced by a creping mechanism, comprising:
positioning, by a computing device, a single light source configured to illuminate a first surface of the creped material by moving the single light source to two or more positions, wherein each position of the two or more positions is characterized by a tilt angle relative to a machine direction (MD) and a crepe direction (CD) of the creped material and a slant angle relative to the surface of the creped material;
obtaining at least two images of an identical portion of the surface of the creped material, each of the at least two images illuminated from a different direction, wherein a first image of the at least two images is illuminated from a first position of the two or more positions and a second image of the at least two images is illuminated from a second position of the two or more positions;
approximating, by the computing device, from the at least two images at least two surface normal vectors corresponding, respectively, to at least two portions of the surface of the creped material;
converting, by the computing device, the at least two surface normal vectors to generate a machine direction gradient image;
analysing, by the computing device, the gradient image to characterize a topography of the surface of the creped material, wherein analysing comprises:
computing, by the computing device, a two dimensional Fourier transform from the gradient image;
computing, by the computing device, a two dimensional power spectrum from the two dimensional Fourier transform; and
smoothing the two dimensional power spectrum to generate a smoothed two dimensional power spectrum; and causing information associated with a characterization of the topography of the surface of the creped material to be rendered in a display device, wherein the information comprises the smoothed two dimensional power spectrum; and
adjusting control of the creping mechanism based on the characterization of the topography.

31. A system for characterizing a surface topology of a creped material produced by a creping mechanism, comprising:
a lighting system, comprising one or more light sources configured to illuminate a first surface from four or more positions, wherein each position of the four or more positions is characterized by a tilt angle relative to a machine direction (MD) and a crepe direction (CD) of the creped material and a slant angle relative to a first surface of the creped material;
at least one computing device; and
program instructions executable in the at least one computing device that, when executed, cause the at least one computing device to:
direct light onto the first surface of a creped material from at least a first position of the four or more positions and a second position of the four or more positions;
obtain at least two images of an identical portion of the creped material, each of the at least two images illuminated from a different direction;
approximate from the at least two images at least two surface normal vectors corresponding, respectively, to at least two portions of the surface of the creped material;
convert the at least two surface normal vectors to generate a machine direction gradient image;
analyse the machine direction gradient image to characterize a topography of the surface of the creped material by:
computing a two dimensional Fourier transform from the gradient image;
computing a two dimensional power spectrum from the two dimensional Fourier transform; and
smoothing the two dimensional power spectrum to generate a smoothed two dimensional power spectrum; and
render in a display device information associated with a characterization of the topography of the surface of the creped material, wherein the information comprises the smoothed two dimensional power spectrum; and
adjust control of the creping mechanism based on the characterized topography.

* * * * *